US008855781B2

(12) United States Patent
Doerr

(10) Patent No.: US 8,855,781 B2
(45) Date of Patent: Oct. 7, 2014

(54) REMOTELY PROGRAMMABLE PERSONAL DEVICE AND SYSTEM AND METHOD FOR REMOTE PROGRAMMING OF A PERSONAL DEVICE

(75) Inventor: Thomas Doerr, Berlin (DE)

(73) Assignee: BIOTRONIK CRM Patent AG (CH)

( * ) Notice: Subject to any disclaimer, the term of this patent is extended or adjusted under 35 U.S.C. 154(b) by 1641 days.

(21) Appl. No.: 12/168,330

(22) Filed: Jul. 7, 2008

(65) Prior Publication Data

US 2009/0043353 A1 Feb. 12, 2009

(30) Foreign Application Priority Data

Aug. 11, 2007 (DE) .......................... 10 2007 037 947

(51) Int. Cl.
A61N 1/08 (2006.01)
A61N 1/372 (2006.01)
G06F 19/00 (2011.01)

(52) U.S. Cl.
CPC ........ G06F 19/3418 (2013.01); A61N 1/37252 (2013.01); G06F 19/3406 (2013.01); A61N 1/08 (2013.01); G06F 19/3412 (2013.01)
USPC ................................. 607/60; 607/30; 607/31

(58) Field of Classification Search
CPC ........... A61N 1/37252; A61N 1/37258; A61N 1/37264; A61N 1/3727; A61N 1/37276; A61N 1/37282; A61N 1/37288; G06F 19/3418; G06F 19/3412; G06F 19/3406; A61B 5/0002; A61B 5/0022; A61B 5/0024

USPC ................................................. 607/30, 31, 60
See application file for complete search history.

(56) References Cited

U.S. PATENT DOCUMENTS

| 5,899,931 | A | 5/1999 | Deschamp et al. |
| 6,363,282 | B1 | 3/2002 | Nichols et al. |
| 6,497,655 | B1 | 12/2002 | Linberg et al. |
| 2003/0041866 | A1 | 3/2003 | Linberg et al. |
| 2003/0149459 | A1* | 8/2003 | Von Arx et al. ................. 607/60 |
| 2004/0030260 | A1* | 2/2004 | Arx ............................... 600/549 |
| 2004/0122295 | A1 | 6/2004 | Hatlestad et al. |
| 2005/0159787 | A1 | 7/2005 | Linberg et al. |
| 2005/0203582 | A1* | 9/2005 | Healy et al. ..................... 607/31 |
| 2006/0111759 | A1 | 5/2006 | Hoyme et al. |
| 2006/0116744 | A1* | 6/2006 | Von Arx et al. ................. 607/60 |
| 2006/0122863 | A1 | 6/2006 | Gottesman et al. |
| 2009/0076570 | A1 | 3/2009 | Hoyme et al. |
| 2009/0132008 | A1 | 5/2009 | Snitting et al. |

FOREIGN PATENT DOCUMENTS

| EP | 10 48 323 A2 | 11/2000 |
| WO | WO 01/43823 A1 | 6/2001 |
| WO | WO 2006/130060 A1 | 12/2006 |

* cited by examiner

Primary Examiner — Tammie K Heller
(74) Attorney, Agent, or Firm — Craig A. Fieschko, Esq.; DeWitt Ross & Stevens S.C.

(57) ABSTRACT

A remotely programmable personal device, in particular a programmable implantable medical device, e.g., a cardiac pacemaker, a defibrillator, a cardioverter or the like. A system for remote programming of such a personal medical device and a method for remote programming of a programmable personal device.

20 Claims, 2 Drawing Sheets

REMOTELY PROGRAMMABLE PERSONAL DEVICE AND SYSTEM AND METHOD FOR REMOTE PROGRAMMING OF A PERSONAL DEVICE

FIELD OF THE INVENTION

The invention relates to a remotely programmable personal device, in particular a programmable implantable medical device, e.g., a cardiac pacemaker, a defibrillator, a cardioverter or the like. Furthermore, the invention relates to a system for remote programming of such a personal medical device and a method for remote programming of a programmable personal device.

BACKGROUND OF THE INVENTION

Medical, physiological or operational data obtained by a cardiac pacemaker or defibrillator is sometimes transmitted to a central service center for the data to be analyzed, and made available to an attending physician via an appropriate user interface.

Some functions of such implants are controlled by software or firmware and are therefore programmable. The implants therefore have a programmable controller for controlling these functions.

It often happens that after initial programming—which may occur shortly before, during or after implantation of the implant—additional programming or reprogramming is useful to better adjust the implant to possible changes in the health of a patient occurring in the meantime, or to otherwise improve the performance of the implant. Such programming or reprogramming often occurs by the physician's establishment of a short-range wireless data link to a particular implant with the help of a programming device, with the physician thereafter programming the implant in the presence of the patient.

However, programming or reprogramming of an implant may instead be done from a remote location, e.g., via the central service center. To this end, a data link may be established between the service center and a intermediate patient device. The intermediate patient device is usually in the vicinity of the patient and serves more or less as a relay station between the implant and the service center. Therefore, the intermediate patient device has two different bidirectional data communication interfaces to allow a bidirectional data communication with the implant at one end and a bidirectional data communication with the service center at the other end. The data communication interface for the connection between the intermediate patient device and the service center may be designed for wireless or wired connection, e.g., via a cellular phone network or via a landline telephone network.

Whereas traditional programming of an implant is performed with the help of a programming device by a physician in the presence of the patient, the physician does not see the patient in remote programming. The physician does not have the patient directly in front of him when performing the remote programming and therefore cannot respond as easily to direct statements by the patient.

It is preferable that this circumstance should be taken into account in designing the implant and in arranging for remote programming of the implant.

SUMMARY OF THE INVENTION

In a preferred version of the invention, the programmable personal device has a first data communication interface for wireless data transmission between the programmable personal device—e.g., the implant—and a programming unit for programming the personal device from the immediate vicinity. In addition, the programmable personal device has a second data communication interface for wireless data transmission, which allows remote programming of the personal device and is different from the first data communication interface (for example, with regard to the data transmission technique or the data format). The programmable personal device may therefore receive programming instructions via the first or second data communication interface, wherein the programming instructions take the form of data containing control parameters that determine the functioning of the personal device via a programmable controller of the personal device. The sum of the control parameters can also be referred to as a program or a control program for the personal device. The personal device may be set up so that only a portion of the control parameters that determine the personal device's functionality can be programmed or altered by programming.

The programmable controller is at least indirectly connected to the two data communication interfaces, and it is also connected to a memory in which multiple control parameters, control parameter combinations, or control parameter attributes can be stored. The control parameter attributes may include, for example, characterizations which denote whether or not a particular control parameter can be varied by remote programming. The programmable controller is designed to receive programming instructions over the first data communication interface for the connection of the personal device to the programming unit, with the programming instructions containing specifications about allowed parameter ranges for one or more control parameters, control parameter attributes for one or more control parameters, or multiple alternative control parameter combinations. A programming instruction may also contain a combination of these control parameters, control parameter attributes or control parameter combinations. This type of programming instruction differs from conventional programming instructions inasmuch as the programming instruction does not (or does not exclusively) contain data or instructions that lead to a direct change in the control parameters, and thus to reprogramming of the personal device. Instead, the personal device is set up for remote programming by such a programming instruction. To do so, the programmable controller is designed to process programming instructions that are received over the first data communication interface and store the parameter ranges, control parameter attributes or control parameter combinations therein in the memory. When a programming instruction is received via the second data communication interface, the programmable controller checks on whether the control parameters and control parameter combinations contained in this programming instruction are compatible with the parameter ranges or control parameter combinations stored in the memory, and it executes a programming instruction received over the second data communication interface (the data communication interface for remote programming) only when this is the case. Execution of such a programming instruction means that the control parameters contained in the programming instruction received via the second data communication interface are stored in the personal device in such a way that after the execution of the programming instruction, they determine the control of the functions of the personal device. The personal device may also receive a programming instruction over the first data communication interface such that no check is performed to ascertain whether the control parameters or control parameter combinations contained in the programming instruction are compatible with the control parameters or control parameter combinations stored in the memory.

The memory thus also contains, in addition to the control parameters that determine the function of the programmable controller, other information, such as parameter ranges, control parameter combinations or control parameter attributes which define whether and how a particular control parameter can be programmed or reprogrammed as part of the remote programming. A control parameter attribute may be set, for example, so that it is impossible to reprogram the corresponding control parameter by remote programming (i.e., by a programming instruction received via the second data communication interface).

The programmable device, and in particular its programmable controller, may also be designed to store various possible control parameter combinations in addition to the particular control parameter combination currently being used. These alternative control parameter combinations may then be activated via a programming instruction. To do so, a combination identifier may be assigned to such control parameter combinations, so that the programming instruction need not explicitly contain all the control parameters of the control parameter combination but instead may contain only the particular combination identifier as a reference to the control parameter combination to be used in the future.

In this context, it is advantageous if the programmable controller is designed to send the parameter ranges, control parameter attributes or control parameter combinations stored in the memory to an external device. This is advisable in particular when a combination identifier is also assigned to a particular control parameter combination. This enables an external device such as a programming device and the physician using such an external device to retrieve such control parameter combinations in a targeted manner, or to observe allowed parameter ranges preselected for the remote programming as stored in the memory of the personal device.

With respect to checking a (remote) programming instruction received via the second data communication interface, there are two alternatives that are equally advantageous, depending on the situation.

First, the programmable controller may be designed to execute a programming instruction received via the second data communication interface only when all the control parameters contained therein are allowed for remote programming and/or are within a parameter range allowed for remote programming, as stored in the memory of the personal device. As soon as only one control parameter contained in the programming instruction is not allowed for remote programming per control parameter attribute or is outside a parameter range allowed for remote programming, the entire programming instruction is not executed. This makes it possible to prevent the control parameters, which are usually carefully coordinated with one another, from being inconsistent in their effective combination after execution of the programming instruction.

Alternatively, the programmable controller may also be designed so that it executes a programming instruction received via the second data communication interface only partially when one or more of the control parameters contained in the programming instruction are outside of the control parameter range allowed for remote programming, or are not allowed for remote programming per the control parameter attribute.

Alternatively, the programmable controller may also be designed to combine the two alternatives in the sense that a few essential control parameters can be reprogrammed together only in combination while other control parameters may also be reprogrammed individually.

As already mentioned, the personal device is preferably an active medical implant, in particular an implantable cardiac pacemaker or an implantable defibrillator/cardioverter. In any case, the second data communication interface for remote programming of the personal device is preferably an interface for wireless data communication with a range of up to five meters and corresponds in particular to the Medical Implant Communications Service Specification (MICS).

The invention also involves a system for remote programming of a programmable personal device which has a personal device of the type described above, as well as a service center for programming the personal device. The service center has at least one data communication interface for at least indirect connection of the service center to the personal device. In addition, the service center is designed to store at least parameter ranges, control parameter attributes or control parameter combinations for the programmable controller of the personal programmable device. The service center has a programming unit for programming the personal device from a distance, with the programming unit being designed to generate a user interface for remote programming of the personal device and to display the parameter ranges or control parameter combinations stored in the memory of the service center for this personal device on this interface for compiling a programming instruction for the personal programmable device.

The service center is preferably also designed for receipt of data packets containing control parameter attributes, control parameter ranges or control parameter combinations by the programmable personal device and to store them in the memory.

The programming unit is preferably designed so that it allows compilation of only programming instructions that contain control parameters compatible with the parameter ranges or control parameter combinations stored in the memory of the service center. In this way, at the time of compiling a programming instruction, a physician is prevented from compiling such a programming instruction that cannot be executed by the implant (i.e., the personal device). It should be pointed out here that the programming unit is usually comprised of a central processing unit (CPU) and a program stored in the memory of the service center.

Where control parameters that are already coordinated with one another in the memory of the personal device are stored in such a manner that they are combined with control parameter combinations and are identified by a combination identifier, it is advantageous if the programming unit of the service center is designed to display the control parameter combinations that have already been stored on the user interface generated for remote programming of the personal device. A physician may then select one of the displayed control parameter combinations and in this way compile the programming instruction. The programming unit is then also designed to add a combination identifier that characterizes the control parameter combination selected by the physician to a corresponding programming instruction. This allows especially simple and efficient programming of the personal device.

The invention further involves a method for remote programming of a programmable personal device. This method comprises at least the steps of:

storing control parameter attributes assigned to programmable control parameters in the personal device, querying stored control parameter attributes during processing of a programming instruction by the personal device, and storing control parameters contained in a programming instruction if these parameters are characterized as alterable by the respective programming instruction via the control parameter attributes.

Alternatively or additionally, the method may comprise the following steps:

storing one or more control parameter combinations and a combination identifier assigned unambiguously to a particular control parameter combination in the personal device, and programming the personal device with the control parameter combination identified by a combination identifier received with a programming instruction after receipt of the programming instruction.

BRIEF DESCRIPTION OF THE DRAWINGS

Exemplary versions of the invention will now be explained in greater detail with reference to the figures, in which.

DETAILED DESCRIPTION OF PREFERRED VERSIONS OF THE INVENTION

A system for remote programming of a personal device 10 in the form of an implant comprises, in addition to the implant 10, a programming device 20, with which the implant 10 can be programmed directly. This is shown on the right side of FIG. 1 by the diagram of the implant 10' in the vicinity of the programming device 20.

Figure 1:
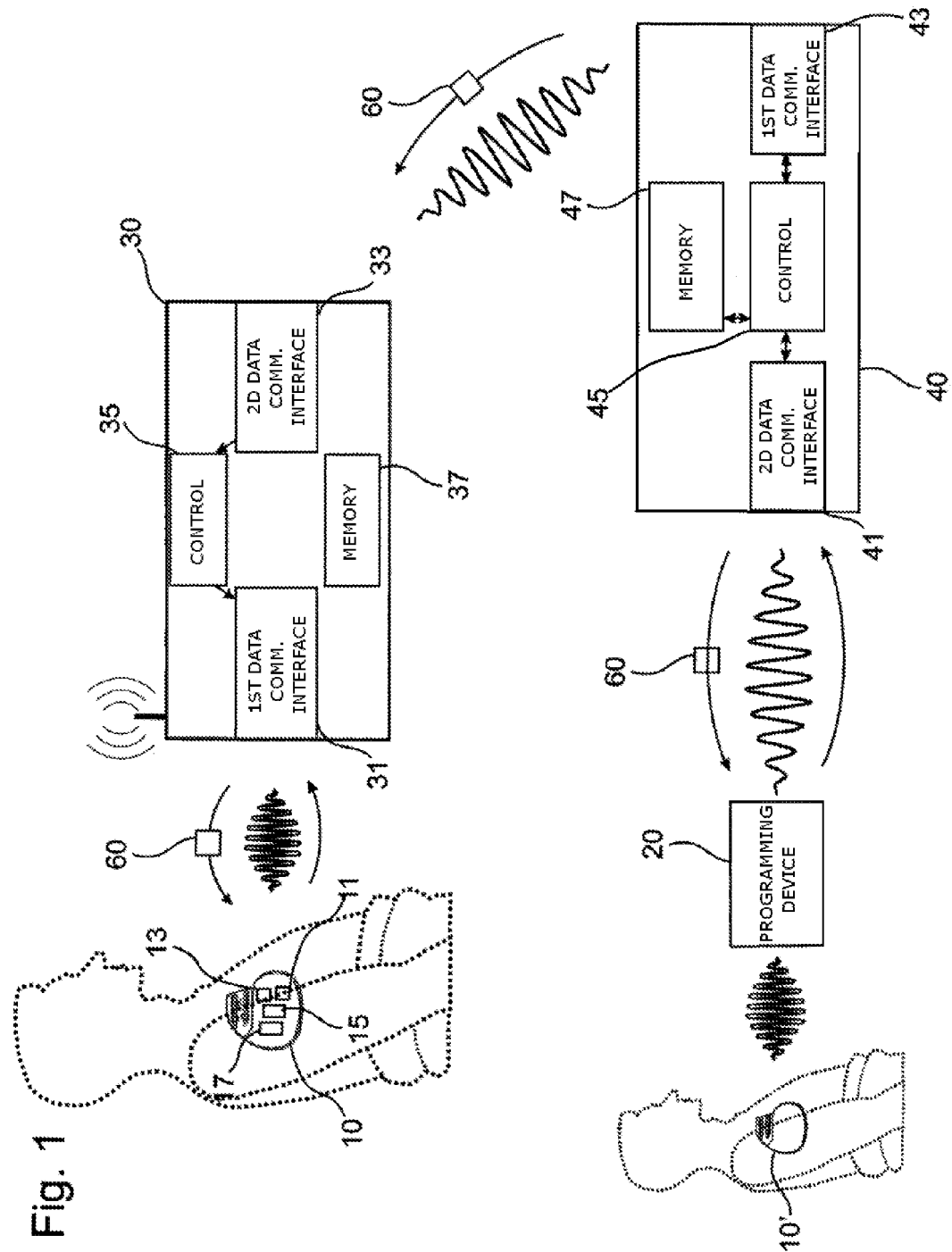
FIG. 1 shows a system for remote programming of a personal device in the form of an implant.

Furthermore, for remote programming of the implant 10, the system comprises a intermediate patient device 30 and a service center 40. As shown in FIG. 1, the programming device 20 may also be used for remote programming of the implant 10 by connecting the programming device 20 to the service center 40.

The implant 10 (see also FIG. 2) has a first data communication interface 11, which allows wireless data communication with the programming device 20. Furthermore, the implant 10 has a second data communication interface 13, which allows wireless data communication with the intermediate patient device 30 and is based on a different wireless technology than the data communication interface 11. Both data communication interfaces 11 and 13 are connected to a programmable controller 15 of the implant 10, which is in turn connected to the memory 17.

The intermediate patient device 30 also has a first data communication interface 31 for wireless data exchange with the implant 10 via its second data communication interface 13. Furthermore, the intermediate patient device 30 also has a second data communication interface 33 which is designed to establish a data link to the service center 40. The first and second data communication interfaces 31 and 33 of the intermediate patient device 30 are interconnected at least indirectly via a control unit 35 of the intermediate patient device 30. In addition, the intermediate patient device 30 has its own memory 37 in which data can be stored temporarily if they have been received by the service center 40, for example, but have not yet been transmitted further to the implant 10.

The service center 40 also has a first data communication interface 43 which serves to provide data communication with the intermediate patient device 30. The data link between the second data communication interface 33 of the intermediate patient device 30 and the first data communication interface 43 of the service center 40 may be accomplished via a hardwired connection, e.g., using a landline telephone network.

The service center 40 also has a control unit 45 and a memory 47 connected to it. The control unit 45 and the memory 47 in combination with one another also constitute a programming unit for remote programming of the implant 10. The control unit 45 and the memory 47 of the service center 40 are designed so that they can generate a user interface for remote programming of the implant 10, allowing a user to compile a programming instruction for the implant 10. To this end, the service center 40 may be connected via the Internet, for example, to a physician's computer on whose display screen the user interface for remote programming of the implant is then displayed.

Figure 2:
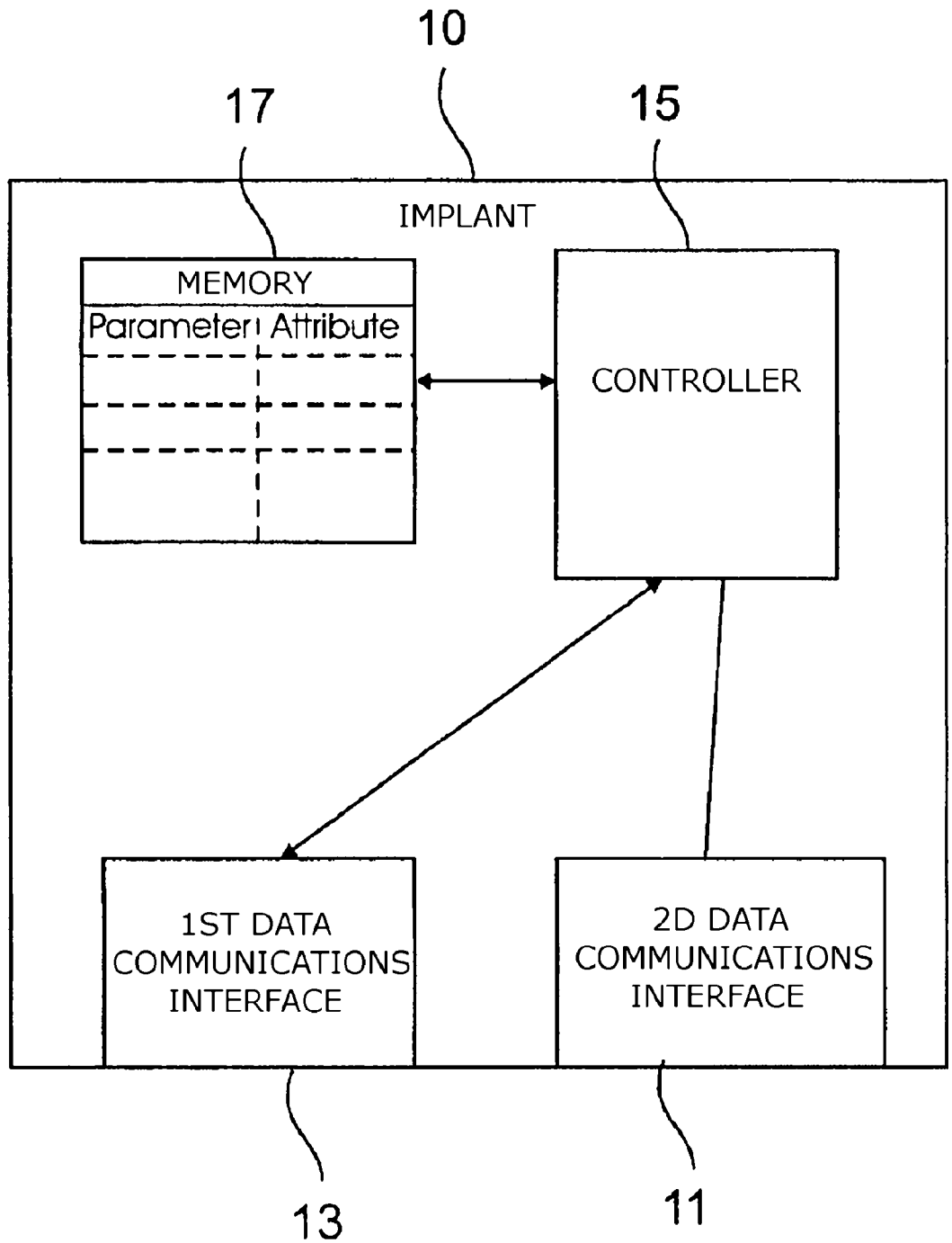
FIG. 2 shows an remotely programmable personal device.

As shown in FIG. 2 in particular, the memory 17 of the implant 10 in combination with the controller 15 is organized so that, in addition to storing parameters currently needed for control of the implant 10, it also stores the control parameter attributes and optionally also the control parameter ranges assigned to these parameters, in addition to storing the parameters currently needed for control of the implant. The control parameters themselves stored in the memory 17 determine the functioning of the controller 15 and thus of the implant 10. The control parameter attributes and the control parameter ranges determine the behavior of the implant in remote programming, in which the implant 10 receives a programming instruction 60 via the second data communication interface 13.

The control parameter attributes and control parameter ranges stored in the memory 17 may be altered only via a direct data link between the implant 10' and the programming device 20, as shown in the lower right of FIG. 1. The control parameter attributes and control parameter ranges cannot be altered by remote programming.

The controller 15 of the implant 10 is designed so that it allows a change in the control parameters stored in the memory 17 with the help of a programming instruction 60 only when the control parameter attribute belonging to the respective control parameter is set so that it allows remote programming. In the simplest case, the control parameter attribute is a single bit, which is either set and then allows remote programming via the data communication interface 13; or the bit is not set and remote programming of this control parameter via the second data communication interface 13 is impossible.

In the same sense, the programmable controller 15 of the implant 10 is designed so that it allows alteration of the control parameters by remote programming only within the parameter range which is stored in the memory 17.

To allow appropriate remote programming of the implant 10, the controller 15 of the implant in conjunction with the memory 17 is designed to transmit the respective control parameters, control parameter attributes and control parameter ranges stored in the memory 17 via the second data communication interface 13 to the service center 40, where these values are stored in the memory 47 of the service center and are used by the control unit 45 of the service center to generate a user interface for the remote programming. The control parameters and control parameter ranges released for remote programming are displayed on the user interface. This is preferably done in the form of a graphical user interface, which can be operated via a graphical input means such as a mouse. A physician can then click on the desired parameters within the displayed parameter ranges and thus compile a programming instruction 60 for the implant 10.

Since one service center 40 will usually take care of multiple implants, the corresponding control parameter attributes and control parameter ranges for the various implants are each stored separately in the memory 47 of the service center 40. Before compiling a programming instruction for a respective implant, the desired implant must first be selected so that the control parameter attributes and control parameter ranges in effect for this implant can then be displayed.

Additionally or alternatively, control parameter combinations which represent a combination of mutually assigned control parameters may also be stored in the memory 17 of the implant 10. A combination identifier unambiguously assigned to the respective control parameter combination is stored in the memory 17 for each control parameter combination.

The implant 10 also transmits these values—control parameter combination and combination identifier—to the service center 40 when the occasion arises.

The service center 40—or more precisely, its control unit 45 in combination with its memory 47—is designed to display control parameter combinations stored in the memory 17 of the implant 10 on the generated graphical user interface. A physician may then select a control parameter combination of interest by clicking on it. The control unit 45 of the service center 40 then generates a programming instruction containing the combination identifier assigned to the selected control parameter combination and transmits this programming instruction to the implant 10.

In the implant 10, the programmable controller 15 and the memory 17 form a program selector that transmits the corresponding control parameter combination stored in the memory 17 of the implant 10 on the basis of the received combination identifier to the corresponding locations in the memory 17 so that the respective control parameters henceforth determine the functioning of the implant 10.

What is claimed is:

1. A programmable personal device (10) including:
   a. first and second data communication interfaces (11, 13):
      (1) configured to wirelessly receive programming instructions including one or more of:
         (a) control parameters defining functionality of the personal device (10),
         (b) allowable parameter ranges for one or more of the control parameters, and
         (c) control parameter attributes defining whether and/or how one or more of the control parameters may thereafter be varied within the personal device (10);
      (2) wherein the second data communication interface (13) utilizes at least one of:
         (a) a different data format, and
         (b) a different data transmission technology,
         than the first data communication interface (11);
   b. a memory (17) configured to store at least a portion of the programming instructions received by the first data communication interface (11),
   c. a programmable controller (15) configured to receive programming instructions from the second data communication interface (13), wherein control parameters within the programming instructions thereafter define the functionality of the programmable controller (15) if these control parameters are in correspondence with the programming instructions from the first data communication interface (11) stored in the memory (17).

2. The programmable personal device (10) of claim 1 wherein the first data communication interface (11) is configured to wirelessly receive its programming instructions from a programming unit (20) separate from the personal device (10).

3. The programmable personal device (10) of claim 2 wherein the second data communication interface (13) is configured to wirelessly receive its programming instructions from the programming unit (20) via an intermediate patient device (30) which
   a. is separate and remotely located from the programming unit (20), and
   b. wirelessly provides the programming instructions from the programming unit (20) to the first data communication interface (11).

4. The programmable personal device (10) of claim 2 wherein the programmable controller (15), after receiving programming instructions from the second data communication interface (13), is configured to only use any control parameters therein to thereafter define the functionality of the programmable controller (15) if these control parameters are in correspondence with any allowable parameter ranges and/or control parameter attributes within the programming instructions previously wirelessly received by the first data communication interface (11) from the programming unit (20).

5. The programmable personal device (10) of claim 1 wherein:
   a. the programming instructions received by the first data communication interface (11) and stored in the memory (17) further include one or more combinations of control parameters, each combination being identified by a combination identifier,
   b. the second data communication interface (13) is configured to receive programming instructions specifying one or more of the combinations of control parameters by their combination identifiers.

6. The programmable personal device (10) of claim 1 wherein the programmable controller (15) is configured to find the control parameters received by the programmable controller (15) from the second data communication interface (13) to be in correspondence with the programming instructions from the first data communication interface (11) stored in the memory (17), and to thereby define the functionality of the programmable controller (15) thereafter, only when all of the control parameters received by the programmable controller (15) are in agreement with any
   a. control parameters,
   b. allowable parameter ranges, and
   c. control parameter attributes,
   within the programming instructions from the first data communication interface (11) stored in the memory (17).

7. A programmable implantable medical device (10) including:
   a. a first data communication interface (11) configured to provide wireless reception of data which contain programming instructions;
   b. a second data communication interface (13) configured to provide wireless reception of data which contain programming instructions, wherein the second data communication interface (13) utilizes at least one of a different data format or data transmission technology than the first data communication interface (11);
   c. a memory (17) configured to store control parameters and/or control parameter attributes,
   d. a programmable controller (15):
      (1) configured to control functions of the medical device (10) in dependence on control parameters, (2) being at least indirectly connected to the first and second data communication interfaces (11, 13),
(3) configured to receive programming instructions from the first data communication interface wherein these received programming instructions:
   (a) are stored in the memory (17), and
   (b) contain a specification of one or more of:
      i. allowed parameter ranges for one or more control parameters,
      ii. control parameter attributes for one or more control parameters, and
      iii. several alternative control parameter combinations;
(4) configured to receive programming instructions over the second data communication interface (13), and execute the programming instructions received over the second data communication interface (13) when any control parameters or control parameter combinations contained therein correspond to the allowed parameter ranges or control parameter combinations stored in the memory (17).

8. The implantable medical device (10) of claim 7 wherein the programmable controller (15) is configured to send parameter ranges, control parameter attributes or control parameter combinations stored in the memory (17) to an external device.

9. The implantable medical device (10) of claim 8 wherein the programmable controller (15) is configured to:
   a. store a combination identifier characterizing a control parameter combination in the memory (17), and send the combination identifier over the second data communication interface (13) to the external device, and
   b. upon receiving programming instructions over the second data communication interface (13) wherein the received programming instructions contain the combination identifier, execute the received programming instructions such that the control parameter combination characterized by the combination identifier thereafter controls the function of the medical device (10).

10. The implantable medical device (10) of claim 8 wherein the programmable controller (15) is configured to store a control parameter attribute corresponding to one or more of the control parameters, wherein each control parameter attribute defines whether the corresponding control parameter is alterable during execution of a programming instruction received over the second data communication interface (13).

11. The implantable medical device (10) of claim 10 wherein the programmable controller (15), after receipt of a programming instruction over the second data communication interface (13) instructing that a control parameter be altered, is configured to query the corresponding control parameter attribute and alter the control parameter only if the corresponding control parameter attribute defines that the control parameter is alterable.

12. The implantable medical device (10) of claim 10 wherein the programmable controller, after receipt of a programming instruction over the second data communication interface (13) instructing that all control parameters be altered, is configured to:
   a. query the corresponding control parameter attributes, and
   b. execute the programming instruction only if the corresponding control parameter attributes define the control parameters as being alterable when received by the second data communication interface (13).

13. The implantable medical device (10) of claim 7 wherein the medical device (10) is an implantable cardiac pacemaker or defibrillator/cardioverter.

14. A system including the implantable medical device (10) of claim 7 and a service center (40) for programming the medical device (10) from a distance, wherein the service center includes:
   a. a data communication interface (43) configured to provide at least indirect connection of the service center to the medical device (10),
   b. a memory (47) configured to store one or more of:
      (1) parameter ranges,
      (2) control parameter attributes, or
      (3) control parameter combinations,
      for control parameters of the programmable controller (15) of the implantable medical device (10), and
   c. a programming unit (45, 47) for the medical device (10), wherein the programming unit (45, 47) is configured to generate a user interface for remote programming of the medical device (10) and display on this interface the parameter ranges, control parameter attributes, and/or control parameter combinations stored in the memory (47) of the service center (40).

15. The system of claim 14 wherein the programming unit (45, 47) is configured to only allow compilation of programming instructions that contain control parameters compatible with parameter ranges, control parameter attributes, and/or control parameter combinations stored in the memory (47) of the service center (40).

16. The system of claim 14 wherein the programming unit (45, 47) is configured to:
   a. display control parameter combinations stored in the memory (47) of the service center, and
   b. allow user selection of one of the displayed control parameter combinations, and
   c. subsequently generate a corresponding programming instruction and sends it to the implantable medical device (10).

17. The system of claim 16 wherein the programming unit (45, 47) is configured to add a combination identifier to a programming instruction generated after selection of a control parameter combination, wherein the combination identifier characterizes the selected control parameter combination.

18. A method for use of the system of claim 14, the method including the steps of:
   a. storing in the memory (17):
      (1) one or more control parameter combinations, and
      (2) one or more combination identifiers, each combination identifier being assigned to a respective one of the control parameter combinations,
   b. programming the medical device (10) with the control parameter combination identified by a combination identifier received with a programming instruction after receipt of the programming instruction.

19. A method for remote programming of the implantable medical device (10) of claim 7, the method including the steps of:
   a. storing in the memory (17) control parameter attributes assigned to programmable control parameters,
   b. querying the stored control parameter attributes when a programming instruction is received by the second data communication interface (13),
   c. storing in the memory (17) any control parameters contained in the programming instruction received by the second data communication interface (13), if the control parameters are characterized as variable by the control parameter attributes.

20. A programmable implantable medical device including:
   a. a first data communication interface configured to wirelessly receive programming instructions;
   b. a second data communication interface configured to wirelessly receive programming instructions, wherein the second data communication interface receives the programming instructions utilizing at least one of:
      (1) a different data format, and
      (2) a different data transmission technology,
      than the first data communication interface;
   c. a programmable controller:
      (1) being at least indirectly connected to the first and second data communication interfaces,
      (2) configured to:
         (a) control functions of the medical device in accordance with control parameters,
         (b) receive programming instructions from the first data communication interface, wherein the programming instructions received from the first data communication interface specify acceptability criteria for control parameters,
         (c) receive programming instructions from the second data communication interface, wherein the programming instructions received from the second data communication interface include control parameters,
         (d) compare the control parameters received from the second data communication interface to the acceptability criteria received from the first data communication interface, and
         (e) execute the programming instructions received from the second data communication interface if the control parameters therein are in agreement with the acceptability criteria received from the first data communication interface.

* * * * *